(12) United States Patent
Campbell et al.

(10) Patent No.: US 8,704,006 B2
(45) Date of Patent: Apr. 22, 2014

(54) SKEWED AND MIDDLE ATTACHED LINEAR CHAIN ALKYLPHENOL AND METHOD OF MAKING THE SAME

(75) Inventors: Curtis Bay Campbell, Hercules, CA (US); Cedrick Mahieux, Vallejo, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 251 days.

(21) Appl. No.: 12/965,595

(22) Filed: Dec. 10, 2010

(65) Prior Publication Data
US 2012/0149945 A1 Jun. 14, 2012

(51) Int. Cl.
C07C 37/16 (2006.01)

(52) U.S. Cl.
USPC ........... 568/790; 568/791; 568/792; 568/793; 568/794

(58) Field of Classification Search
USPC .................................. 568/790–794
See application file for complete search history.

(56) References Cited

U.S. PATENT DOCUMENTS

| | | | |
|---|---|---|---|
| 2,073,995 A * | 3/1937 | Raiziss et al. ................. | 568/780 |
| 2,106,760 A * | 2/1938 | Raiziss et al. ................. | 568/780 |
| 2,133,287 A * | 10/1938 | Flett ............................. | 562/82 |
| 2,140,782 A * | 12/1938 | Arnold et al. ................. | 568/785 |
| 3,119,880 A | 1/1964 | Kollar et al. | |
| 3,558,716 A | 1/1971 | Engelhardt et al. | |
| 3,864,407 A | 2/1975 | Yates | |
| 3,919,333 A * | 11/1975 | Wollensak ................... | 568/785 |
| 3,953,538 A | 4/1976 | Boney | |
| 3,979,466 A | 9/1976 | Yates | |
| 4,011,273 A | 3/1977 | Abend et al. | |
| 4,225,737 A | 9/1980 | Mikulicz et al. | |
| 4,283,573 A | 8/1981 | Young | |
| 4,532,368 A | 7/1985 | Swanson | |
| 4,536,301 A | 8/1985 | Malloy et al. | |
| 4,816,185 A | 3/1989 | Parker | |
| 5,750,818 A | 5/1998 | Mehlberg et al. | |
| 6,008,181 A | 12/1999 | Cripe et al. | |
| 6,054,419 A | 4/2000 | Le Coent | |
| 6,551,967 B2 | 4/2003 | King et al. | |
| 6,911,567 B2 | 6/2005 | Both et al. | |
| 6,989,355 B1 | 1/2006 | Campbell et al. | |
| 7,825,055 B2 | 11/2010 | Elomari et al. | |

OTHER PUBLICATIONS

Database CAPLUS on STN, Acc. No. 1924:1611, POTEL, Bulletin des Sciences Pharmacologiques (1923), 30. p. 453-459 (abstract).*
Database CAPLUS on STN, Acc. No. 1937:25082, Niederl, US 2,073,316 (Mar. 9, 1937) (abstract).*
Database CAPLUS on STN, Acc. No. 1961:25598, GB 846695 (Aug. 31, 1960) (abstract).*
Database CAPLUS on STN, Acc. No. 1961:109039, Erich et al., Journal of Applied Polymer Science (1960), 3, p. 296-301 (abstract).*
Database CAPLUS on STN, Acc. No. 1965:90466, Kakhniashvili et al., Soobshcheniya Akademii Nauk Gruzinskoi USSR (1965), 37(3), p. 573-580 (abstract).*
Karakica S.K. et. al., "Peculiarities of extraction of carbonate complexes of trivalent transplutonium elements by alkylpyrocatechols" Radiokhimiya 1987, vol. 29, 335-341.
Rosemarie Szostak's Handbook of Molecular Sieves (New York, Van Nostrand Reinhold, 1992): pp. 100, 132-134, 157-158, 191, 219-221, 243, 256, 265, 294, 299, 304, 343, 377, 379, 409, 410, 419, 420, 453-455, 480, 500, 532, 533, 560, 567, 570, 571, and 583.

* cited by examiner

Primary Examiner — Brian J Davis

(57) ABSTRACT

A process for preparing an alkylated hydroxyl aromatic compound comprising reacting
(a) a hydroxyl aromatic compound (I), having the following structure;

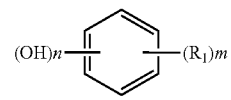

wherein n 1, 2 or 3; m is 0, 1, 2, or 3 and $R_1$ is Hydrogen or hydrocarbyl group;
and
(b) at least one β-branched primary alcohol component in the presence of an alkylating catalyst thereby producing an alkylated hydroxyl aromatic compound.

8 Claims, No Drawings

SKEWED AND MIDDLE ATTACHED LINEAR CHAIN ALKYLPHENOL AND METHOD OF MAKING THE SAME

FIELD OF THE INVENTION

The present invention is directed to skewed and middle attached linear chain alkylphenol compounds and methods of making the same.

BACKGROUND OF THE INVENTION

It is well known to catalyze the alkylation of aromatics with olefins in the presence of a variety of Lewis or Bronsted acid catalysts. Typical commercial catalysts include phosphoric acid/kieselguhr, aluminum halides, boron trifluoride, antimony chloride, stannic chloride, zinc chloride, onium poly (hydrogen fluoride), solid acid catalysts, and hydrogen fluoride. Alkylation with lower molecular weight olefins, such as propylene, can be carried out in the liquid or vapor phase. For alkylations with higher olefins, such as $C_{16+}$ olefins, the alkylations are done in the liquid phase, often in the presence of hydrogen fluoride.

DESCRIPTION OF THE RELATED ART

Cripe et al., U.S. Pat. No. 6,008,181, discloses mid-chain branched primary alkyl alkoxylated sulfate surfactants useful in laundry and cleaning compositions, especially granular and liquid detergent compositions. These surfactant mixtures are also suitable for formulation with other surfactants for the purpose of providing improved surfactant systems, especially for use in detergent compositions which will be used in laundry processes involving low water temperature wash conditions. The present invention also relates to novel mid-chain branched primary alkyl alkoxylated sulfate surfactants suitable for use in the surfactant mixtures.

Mikulicz et al., U.S. Pat. No. 4,225,737, discloses a process for the alkylation of an aromatic hydrocarbon with an olefin-acting alkylating agent. The aromatic hydrocarbon is commingled with a first portion of said alkylating agent in a first alkylation reaction zone at alkylation reaction conditions in contact with a hydrofluoric acid catalyst. Boney, U.S. Pat. No. 3,953,538 discloses an alkylation process in which a stream of an olefinic material is mixed with an acid stream and polymerized to cause formation of a polymeric diluent for the high strength acid which is initially charged to the alkylation process.

Mehlberg et al., U.S. Pat. No. 5,750,818 discloses a process for the liquid phase alkylation in an alkylation reactor of a hydrocarbon substrate with an olefinic alkylating agent in the presence of an acid alkylation catalyst at least one hydrocarbon having a lower boiling point than the hydrocarbon substrate and with a substantial stoichiometric excess of the hydrocarbon substrate over the alkylating agent to form a liquid product mixture.

King et al., U.S. Pat. No. 6,551,967 discloses a low overbased alkaline earth metal alkylaryl sulfonate having a Total Base Number of from aoubt 2 to about 30, a dialkylate content of 0% to about 25% and a monoalkylate content of about 75% to about 90% or more, wherein the alkylaryl moiety is alkyltoluene or alkylbenzene in which the alkyl group is a $C_{15}$-$C_{21}$ branched chain alkyl group derived from a propylene oligomer are useful as lubricating oil additives.

LeCoent, U.S. Pat. No. 6,054,419 discloses a mixture of alkyl aryl sulfonates of superalkalinized alkaline earth metals comprising (a) 50 to 85% by weight of a mono alkyl phenyl sulfonate with a C14 to C40 linear chain wherein the molar proportion of phenyl sulfonate substituent in position 1 or position 2 is between 0 and 13% and (b0 15 to 50% by weight of a heavy alkyl aryl sulfonate, wherein the aryl radical is phenyl or not, and the alkyl chains are either two linear alkyl chains with a total number of carbon atoms of 16 to 40, or one or a plurality of branched alkyl chains with on average a total number of carbon atoms of 15 to 48.

Malloy et al., U.S. Pat. No. 4,536,301 discloses a surfactant slug used to recover residual oil in subterranean reservoirs. The slug comprises a mixture of (1) from about 1 to about 10% of a sulfonate of a mixture of mono- and dialkyl-substituted aromatic hydrocarbon which has been obtained by the alkylation of an aromatic hydrocarbon with an olefinic hydrocarbon in the presence of a hydrogen fluoride catalyst; (2) a lower alkyl alcohol which possesses from about 3 to about 6 carbon atoms; and (3) a nonionic cosurfactant comprising an ethoxylated n-alcohol which possesses from about 12 to about 15 carbon atoms.

Campbell et al., U.S. Pat. No. 6,989,355 discloses an under-neutralized alkylxylene sulfonic acid composition for enhanced oil recovery processes. This invention is also directed to a method for enhancing the recovery of oil from a subterranean reservoir which method employs the underneutralized alkylxylene sulfonic acid compositions of the present invention. The under-neutralized alkylxylene sulfonic acid compositions are employed in an aqueous media. The method optionally employs suitable co-surfactants, such as alcohols, alcohol ethers, polyalkylene glycols, poly (oxyalkylene)glycols and/or poly(oxyalkylene)glycol ethers.

Parker, U.S. Pat. No. 4,816,185 discloses reaction products $C_9$-$C_{30}$ alkylbenzenes with styrene and sulfonated derivatives thereof and processes for preparing such products and derivatives. The sulfonate salts of reaction products are especially useful as detergents.

SUMMARY OF THE INVENTION

In its broadest embodiment, the present invention is directed to

A process for preparing an alkylated hydroxyl aromatic compound comprising reacting (a) a hydroxyl aromatic compound (I), having the following structure;

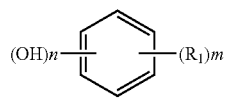

wherein n 1, 2 or 3; m is 0, 1, 2, or 3 and $R_1$ is Hydrogen or hydrocarbyl group.

and (b) at least one β-branched primary alcohol component in the presence of an alkylating catalyst thereby producing an alkylated hydroxyl aromatic compound.

In one embodiment, the invention is directed to an alkylated hydroxyl aromatic compound having the following structure:

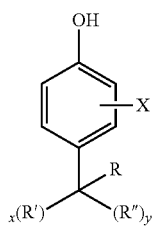

wherein X can be either hydrogen, an aliphatic chain or an hydroxyl group depending on the structure of the aromatic material alkylated and wherein R is methyl and x+y=6 to 48; wherein R' and R" are alkyl, having from about 8 to about 50 carbon atoms.

DETAILED DESCRIPTION OF THE INVENTION

While the invention is susceptible to various modifications and alternative forms, specific embodiments thereof are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DEFINITIONS

The term "hydrocarbyl" refers to an organic radical primarily composed of carbon and hydrogen which may be aliphatic, alicyclic, aromatic or combinations thereof, e.g., aralkyl or alkaryl. Such hydrocarbyl groups may also contain aliphatic unsaturation, i.e., olefinic or acetylenic unsaturation, and may contain minor amounts of heteroatoms, such as oxygen or nitrogen, or halogens, such as chlorine. When used in conjunction with carboxylic fatty acids, hydrocarbyl will also include olefinic unsaturation.

The term "alkyl" refers to both straight- and branched-chain alkyl groups.

One embodiment of the present invention is a process for preparing an alkylated hydroxyaromatic compound comprising (a) reacting at least one hydroxyl-containing aromatic compound with at least one β-branched primary alcohol component that is derived from a primary aliphatic alcohol thereby producing an alkylated hydroxyaromatic compound having at least 65 to 98 weight percent of a para-substituted hydroxy monoalkylated aromatic isomer. The at least one β-branched primary alcohol component that is derived from a primary aliphatic alcohol has from about 8 to about 50 carbon atoms.

Aromatic Compound

The aromatic compound may comprise hydroxyl substituted aromatic compounds and corresponding ether aromatic compounds. The following structure represents the types of aromatic compounds that are employed in the present invention:

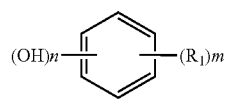

I

Wherein n is 1, 2 or 3; m is 0, 1, 2, or 3 and $R_1$ is Hydrogen or hydrocarbyl group.

Typically, the hydrocarbyl group may be alkyl, aryl, aralkyl, or alkaryl, which may be unsubstituted or substituted with one or more functional groups such as, hydroxy, amino-, halo-, cyano-, carboxyl, or nitro-.

Aromatic compounds (I) that are alkylated in the subject invention may be mono- or di-substituted. Such aromatic compounds in (I) may include trihydroxybenzenes, e.g., pyrogallol, phloroglucinol, and hydroxyquinol, and dihydroxybenzenes, e.g., catechol, resorcinol, hydroquinone, their ether derivatives, and phenol, anisole and cresol, and mixtures thereof, with phenol being the preferred compound.

It is also contemplated that the hydroxyaromatic compounds may include fused hydroxyaromatic compounds, such as naphthol and other phenolic compounds.

The hydroxyaromatic compounds employed in the present invention are prepared by methods that are well known in the art.

Alcohol Component

Sources of Alcohols

The at least one alcohol component employed in the present invention is a β-branched primary alcohol component that may be derived from a primary aliphatic alcohol. These types of alcohols are well known in the art and may include Guerbet-type alcohols, which are derived by methods that are well known and are exemplified in U.S. Pat. No. 6,911,567; U.S. Pat. No. 4,011,273; U.S. Pat. No. 3,119,880; U.S. Pat. No. 3,558,716; U.S. Pat. No. 3,979,466; U.S. Pat. No. 3,864,407. These β-branched primary alcohol components may also be purchased from such companies as Jarchem Industries, Newark, N.J.

It is contemplated that tertiary alcohols may also be employed in the present invention.

In one embodiment, the β-branched primary alcohol component comprises from about 8 to about 50 carbon atoms. More preferably, the β-branched primary alcohol component comprises from about 12 to about 40 carbon atoms. Most preferred, the β-branched primary alcohol component comprises from about 12 to about 20 carbon atoms. Alcohols, including but not limited to, that may be employed are 2-n-butyl-1-n-octanol and 2-n-octyl-1-n-dodecanol:

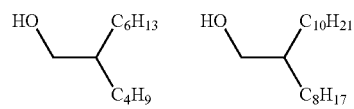

Typically these alcohols have the following general structure:

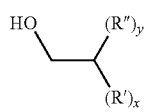

Wherein R' and R" are hydrocarbyl groups; wherein x and y represent the number of carbons present in the hydrocarbyl moeity and 6≤x+y≤48.

Alkylating Catalyst

The alkylation of the aromatic compound is carried out in the presence of at least one of several types of alkylating catalysts.

In one embodiment, the alkylating catalyst is an acidic catalyst, which may be selected from the group consisting of natural zeolites, synthetic zeolites, synthetic molecular sieves, clays, and ion exchange resins. Examples include a catalyst that comprises the acid forms of an acidic clay, or an acidic molecular sieve or a zeolite having an average pore size of at least 6.0 angstroms. Such zeolites include Y zeolite, beta, SSZ-25, SSZ-26, and SSZ-33. Other possible catalysts include L zeolite, mordenite, boggsite, cloverite, VPI-5, MCM-41, MCM-36, SAPO-8, SAPO-5, MAPO-36, SAPO40, SAPO-41, MAPSO-46, CoAPO-50, hexagonal faujasite (EMC-2), gmelinite, mazzite (omega zeolite), offretite, ZSM-18, ZSM-12, Amberlyst® 36 and Amberlyst® 70. Some of these catalysts are discussed in Rosemarie Szostak's Handbook of Molecular Sieves (New York, Van Nostrand Reinhold, 1992).

An acid catalyst comprising Y zeolite may be employed in the present invention and has a silica to alumina ratio of at least 40:1, and preferably, 60:1.

Useful acidic clays may be derived from naturally occurring or synthetic materials. One skilled in the art would realize that there are a number of such clays that are known to be alkylation catalysts. Examples of such acidic clays include montmorillonite, laponite, and saponite. Pillared clays may also be used as catalysts.

In one embodiment, the alkylating catalyst is a zeolite catalyst having a controlled macropore structure comprising either Y zeolite or mordenite zeolite or mixtures thereof.

The catalysts of the present invention may be shaped or formed into tablets, extrudates or any other shape, such as beads, using procedures well known in the prior art. The preparation of extrudates requires the presence of a binder, such as alumina. The tabletted catalysts do not require the presence of a binder, but a binder may be present in a tabletted zeolite catalyst. The crystalline zeolite powder may be compressed to form a tablet.

The alkylation of aromatic hydrocarbons, as defined hereinabove, may be carried out in a fixed bed reactor in the presence of the catalysts employed in the present invention.

In one embodiment, the alkylating catalyst may include a solid catalyst comprising a sulfonic acid resin catalyst or an acidic clay. The sulfonic acid resin catalyst is an anionic ion exchange resin, such as, but not limited to, Amberlyst 70 or Dowex M-31, which are sold by Rohm and Haas Co. Acidic clays such as Filtrol-24 can also be used. The catalyst is employed in an amount sufficient to catalyze the alkylation of the hydroxyl-containing aromatic compound. Typically, when the alkylation takes place in batch mode, the amount of catalyst used will be about 1 wt. % to about 50 wt. %, based on the weight of the total charge (i.e., the reaction mixture which contains the aromatic compound, alcohol, and catalyst).

In one embodiment, the alkylating catalyst is an ionic liquid catalyst. Specifically, the alkylating catalyst is an acidic ionic liquid catalyst.

The acidic ionic liquid catalyst is composed of two components which form a complex. The first component of the catalyst will typically comprise a compound selected from the group consisting of aluminum halide, alkyl aluminum halide, gallium halide, and alkyl gallium halide. Especially preferred for the first component is aluminum halide or alkyl aluminum halide. In particular, aluminum trichloride may be used as the first component for preparing the catalyst used in practicing the present invention.

The second component making up the ionic liquid catalyst is an organic salt or mixture of salts. These salts may be characterized by the general formula $Q^+A^-$, wherein $Q^+$ is an ammonium, phosphonium, or sulfonium cation and $A^-$ is a negatively charged ion such as $Cl^-$, $Br^-$, $ClO_4^-$, $NO_3^-$, $BF_4^-$, $BCL_4^-$, $PF_6^-$, $SbF_6^-$, $AlCl_4^-$, $ArF_6^-$, $TaF_6^-$, $CuCl_2^-$, $FeCl_3^-$, $SO_3CF_3^-$, $SO_3C_7^-$, and 3-sulfurtrioxyphenyl. Preferred for use as the second component are those quaternary ammonium halides containing one or more alkyl moieties having from about 1 to about 9 carbon atoms, such as, for example, trimethylamine hydrochloride, methyltributylammonium, and 1-butylpyridinium, or hydrocarbyl substituted imidazolium halides, such as for example, 1-ethyl-3-methyl-imidazolium chloride.

The presence of the first component should give the ionic liquid a Lewis acidic character. Generally, the greater the mole ratio of the first component to the second component, the greater the acidity of the ionic liquid mixture. When aluminum trichloride and trimethylamine hydrochloride are used as the first and second components, respectively, of the acidic ionic liquid catalyst, they preferably will be present in a mole ratio of from greater than about 1:1 to about 2:1.

The alkylation process may be carried out in a batch or continuous process. The acidic ionic liquid catalyst may be recycled when used in a continuous process or batch process.

Process for Preparing Alkylated Aromatic Compound

The alkylation of the present invention may be carried out in a batch process or a continuous process.

In one embodiment of the present invention, the alkylation process is carried out by reacting at least one aromatic compound, as defined hereinabove, or a mixture of aromatic compounds with at least one β-branched primary alcohol component in the presence of an alkylating catalyst, as described hereinabove, in a reactor in which agitation is maintained, thereby producing a reaction product. The hydrocarbon product is further treated to remove excess un-reacted hydroxyl-containing aromatic compounds and, optionally, alcohol components from the desired alkylate product.

When an ionic liquid catalyst is employed, then the process may involve the liquid-liquid separation of the aromatic compound and catalyst.

The total charge mole ratio of alkylating catalyst to the β-branched primary alcohol component is about 1.0:0.5 to about 0.1:1.

The total charge mole ratio of the hydroxyl-containing aromatic compound to the β-branched primary alcohol component is about 5:1 to about 0.5:1.

Many types of reactor configurations may be used for the reactor zone. These include, but are not limited to, batch and continuous stirred tank reactors, reactor riser configurations, ebulating bed reactors, and other reactor configurations that are well known in the art. Many such reactors are known to those skilled in the art and are suitable for the alkylation reaction. Agitation is critical for the alkylation reaction and can be provided by rotating impellers, with or without baffles, static mixers, kinetic mixing in risers, or any other agitation devices that are well known in the art.

The alkylation process may be carried out at temperatures from about 60° C. to about 200° C. The process is carried out under sufficient pressure that a substantial portion of the feed components remain in the liquid phase. Typically, a pressure of 0 to 150 psig is satisfactory to maintain feed and products in the liquid phase.

The residence time in the reactor is a time that is sufficient to convert a substantial portion of the β-branched primary alcohol component to alkylate product. The time required is from about 30 minutes to about 5 days. A more precise residence time may be determined by those skilled in the art using batch stirred tank reactors to measure the kinetics of the alkylation process.

The at least one hydroxyl-containing aromatic compound or mixture of hydroxyl-containing aromatic compounds and the mixture of β-branched primary alcohol component may be injected separately into the batch reactor or may be mixed prior to injection into the batch reactor.

Preferably an excess of hydroxyl-containing aromatic compounds is used to increase reaction rate, improve product selectivity, e.g., monoalkylation. When excess hydroxyl-containing aromatic compounds are used, the excess un-reacted hydroxyl-containing aromatic in the reactor effluent can be separated, e.g. by distillation, extraction.

Alkylated Aromatic Compound

The resulting product from the alkylation of an hydroxyaromatic compound is primarily the para-alkyl-substituted hydroxy monoalkylated aromatic isomer having the following structure (II)

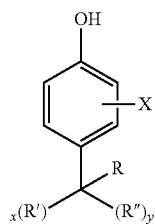

(II)

wherein X can be either a Hydrogen, aliphatic chain or an hydroxyl group depending on the structure of the aromatic material alkylated and wherein R is methyl or hydrogen and when either R is hydrogen, then x+y=7 to 49 or when R is methyl, then x+y=6 to 48; wherein R' and R" are alkyl, having from about 8 to about 50 carbon atoms.

In one embodiment, the hydroxyaromatic compound is phenol, catechol or cresol. In a preferred embodiment, the hydroxyaromatic compound is phenol. The resulting product is a monoalkylated aromatic compound having a mixture of ortho and para isomers wherein the para isomer content is from 65% to about 98%.

Other embodiments will be obvious to those skilled in the art.

The following examples are presented to illustrate specific embodiments of this invention and are not to be construed in any way as limiting the scope of the invention.

EXAMPLES

General Remarks

The following examples of the present invention, were performed under nitrogen atmosphere in a dry three-neck round bottom flask equipped with a reflux condenser and a non-mercury thermometer.

Catalysts

All resin and zeolite catalysts were pre-dried overnight at 120° C. prior to experiments. One of several catalysts was employed. Ionic exchange resin catalysts (Amberlyst-70 and Dowex M-31) were purchased from Rohm & Haas. Y zeolite extrudates were obtained from Chevron Lummus. ZSM-12 is described in U.S. Pat. No. 3,832,449 and was prepared according to that description. SSZ-25 was prepared according to U.S. Pat. No. 5,421,992.

The ionic liquid catalyst was prepared according to U.S. Pat. No. 7,825,055.

β-Branched Primary Alcohols (Guerbet Alcohols)

2-butyl-1-octanol and 2-octyl-1-dodecanol were purchased from Jarchem Industries, Newark, N.J. and used without any further purification.

Hydroxyl-Containing Aromatic Compound

Phenol was purchased from Sigma-Aldrich, St. Louis, Mo., and used without any further purification.

GC/MS chromatograms were recorded on an Agilent 5952 using a non-polar column. The general alkylation procedure was to add the desired amount of catalyst to a mixture of 4 equivalents of phenol and 1 equivalent of Guerbet-type alcohol pre-heated at the desired reaction temperature. The reaction was monitored by GC in order to determine the mixture product distribution as well the reaction advancement.

Experimental Procedures

Example 1

C12 Guerbet-Type Alcohol and Amberlyst 70 a) According to the general reaction procedure, 1.60 mL (17.63 mmol) of phenol was reacted at 100° C. for 24 hours with 1 mL (0.833 g; 4.47 mmol) of 2-butyl-1-octanol in the presence of 279 mg (10% wt.) of Amberlyst 70 yielding 85% para-substituted isomer as determined by GC.

b) According to the general procedure, 1.99 g (17.88 mmol) of catechol was reacted at 100° C. for 24 hours with 1 mL (0.833 g; 4.47 mmol) of 2-butyl-1-octanol in the presence of 314 mg (10% wt.) of Amberlyst 70 yielding exclusively 1,2,4-substituted isomer as determined by GC. There was 100% conversion of 2-butyl-1-octanol to a monoalkylated hydroxyaromatic.

c) According to the general procedure, 1.88 mL (17.88 mmol) of o-cresol was reacted at 100° C. for 29 hours with 1 mL (0.833 g; 4.47 mmol) of 2-butyl-1-octanol in the presence of 695 mg (20% wt.) of Amberlyst 70 yielding 90% para-substituted isomer minimum (related to the hydroxyl group) as determined by GC. There was 99% conversion of 2-butyl-1-octanol to a monoalkylated hydroxyaromatic.

Example 2

C12-Guerbet-Type Alcohol and Dowex M-31

According to the general reaction procedure, 1.62 mL (17.89 mmol) of phenol was reacted at 110° C. for 24 hours with 1 mL (0.833 g; 4.47 mmol) of 2-butyl-1-octanol in the presence of 281 mg (10% wt.) of Dowex M-31 yielding 14% ortho and 86% para-substituted isomer as determined by GC. There was 100% conversion of 2-butyl-1-octanolto a monoalkylated hydroxyaromatic.

Example 3

C12-Guerbet Type-Alcohol and Faujasite-Type Zeolite, (e.g., Y-zeolite having a Silicon-to-Alumina Ratio 60:1)

(a) According to the general reaction procedure, 1.45 mL (10.06 mmol) of phenol was reacted at 100° C. for 24 hours with 0.9 mL (0.748 g; 4.02 mmol) of 2-butyl-1-octanol in presence of 967 mg (30% wt.) of Y-zeolite extrudates yielding 14% ortho- and 86% para-substituted isomer as determined by GC. There was 66% conversion of the 2-butyl-loctanol to a monoalkylated hydroxyaromatic.

(b) According to the general reaction procedure, 1.62 mL (17.88 mmol) of phenol was reacted at 100° C. for 24 hours with 1.9 mL (0.833 g; 4.47 mmol) of 2-butyl-1-octanol in presence of 2.51 g (50% wt.) of Y-zeolite extrudates yielding 20% ortho- and 80% para-substituted isomer as determined by GC. There was 84% conversion of the 2-butyl-1-octanol to a monoalkylated hydroxyaromatic.

Example 4

C12-Guerbet Type Alcohol and MTW-Type Zeolite (ZSM-12 having a Silicon-to-Alumina Ratio of 80:1)

According to the general reaction procedure, 1.62 mL (17.88 mmol) of phenol was reacted at 100° C. for 57 hours with 1.0 mL (0.833 g; 4.47 mmol) of 2-butyl-1-octanol in presence of 281 mg (10% wt.) of ZSM-12 catalyst yielding greater than 69% para-substituted isomer as determined by GC. There was 48% conversion of the 2-butyl-1-octanol to a monoalkylated hydroxyaromatic.

Example 5

C12-Guerbet-Type Alcohol and MWW Framework-Type Zeolite (SSC-25)

According to the general reaction procedure, 1.45 mL (16.06 mmol) of phenol was reacted at 110° C. for 30 h with 0.9 mL (0.748 g; 4.02 mmol) of 2-butyl-1-octanol in presence of 769 mg (26% wt.) of SSZ-25 catalyst yielding greater than 71% para-substituted isomer as determined by GC. There was 14% conversion of the 2-butyl-1-octanol to a monoalkylated hydroxyaromatic.

Example 6

C12-Guerbet Type-Alcohol and Ionic Liquid Catalyst

In a 3 neck round bottom flask equipped with a reflux condenser 1.62 mL (17.88 mmol) of phenol was reacted at 100° C. for 7 h with 1 mL (0.833 g; 4.47 mmol) of 2-butyl-1-octanol in presence of 1.08 g (4.47 mmol) of n-butyl pyridinium chloride heptachloroaluminate catalyst. The reaction mixture was then cooled down, and poured into ice. The aqueous solution was extracted with dichloromethane (3 times 20 mL), washed with brine, dried over sodium sulfate and concentrated under vacuum yielding the corresponding alkylphenols greater than 95% para substituted isomers as determined by GC and NMR. There was a 95% conversion

Example 7

C20 Guerbet-Type Alcohol and Amberlyst 70 Catalyst

According to the general reaction procedure, 1.08 mL (11.97 mmol) of phenol was reacted at 100° C. for 24 hours with 1 mL (0.911 g; 2.99 mmol) of 2-octyl-1-dodecanol in presence of 878 mg (10% wt.) of Amberlyst 70 yielding 18% ortho- and 82% para-substituted isomer as determined by GC. There was a 100% conversion of the 2-octyl-1-dodecanol to a monoalkylated hydroxyaromatic.

Example 8

C20 Guerbet-Type Alcohol and Amberlyst 70 Catalyst

According to the general reaction procedure, 2.16 mL (23.9 mmol) of Phenol was reacted at 100° C. for 24 h with 2 mL (1.822 g; 5.98 mmol) of 2-octyl-1-dodecanol in presence of 454 mg (10% wt.) Amberlyst 70 yielding greater than 96% para-substituted isomer as determined by GC. There was a 91% conversion of the 2-octyl-1-dodecanol to a monoalkylated hydroxyaromatic.

What is claimed is:

1. A process for preparing an alkylated hydroxyl aromatic compound comprising reacting
    (a) a hydroxyl aromatic compound (I), having the following structure;

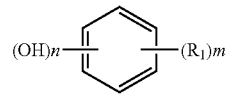

I wherein n 1, 2 or 3; m is 0, 1, 2, or 3 and $R_1$ is Hydrogen or hydrocarbyl group and
    (b) at least one β-branched primary alcohol in the presence of an ionic liquid catalyst or an acidic alkylating catalyst selected from the group consisting of natural zeolites, synthetic zeolites, synthetic molecular sieves, clays, and ion exchange resins, thereby producing an alkylated hydroxyl aromatic compound wherein the alkylated hydroxyl aromatic compound comprises at least about 65 to 98 weight percent of a para-substituted hydroxyl alkylated aromatic isomer.

2. The process according to claim 1 wherein the hydroxyl aromatic compound is phenol.

3. The process according to claim 1 wherein the at least one β-branched primary alcohol has the following structure:

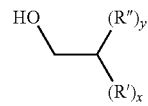

wherein R' and R" are hydrocarbyl groups and wherein x and y represent the number of carbons present in the hydrocarbyl moiety and 6≤x+y≤48.

4. The process according to claim 1 wherein the at least one β-branched primary alcohol comprises from about 8 to about 50 carbon atoms.

5. The process according to claim 4 wherein the at least one β-branched primary alcohol comprises from about 12 to about 40 carbon atoms.

6. The process according to claim 4 wherein the at least one β-branched primary alcohol comprises from about 12 to about 20 carbon atoms.

7. The process according to claim 1 wherein the an acidic catalyst is an ion exchange resin catalyst.

8. The process according to claim 1 wherein the acidic catalyst is a natural zeolite or a synthetic catalyst.

* * * * *